United States Patent [19]
Lang

[11] Patent Number: 5,474,571
[45] Date of Patent: Dec. 12, 1995

[54] MEDICAL FORCEPS WITH JAWS WHICH FIRST TILT AND THEN OPEN

[75] Inventor: Dieter Lang, Stockheim, Germany

[73] Assignee: Karl Storz GmbH & Co., Tuttlingen, Germany

[21] Appl. No.: 194,240

[22] Filed: Feb. 7, 1994

[30] Foreign Application Priority Data

Feb. 24, 1993 [DE] Germany ............... 9302650 U

[51] Int. Cl.⁶ .................................. A61B 17/10
[52] U.S. Cl. ........................... 606/205; 606/174
[58] Field of Search ............... 606/174, 206, 606/208; 30/194

[56] References Cited

U.S. PATENT DOCUMENTS

| | | | |
|---|---|---|---|
| 5,133,735 | 7/1992 | Slater et al. | 606/174 X |
| 5,171,256 | 12/1992 | Smith et al. | 606/205 |
| 5,219,354 | 6/1993 | Choudhury et al. | 606/174 |
| 5,290,308 | 3/1994 | Knight et al. | 606/205 |

FOREIGN PATENT DOCUMENTS

9115760  12/1991  Germany ............... A61B 17/28

*Primary Examiner*—Stephen C. Pellegrino
*Assistant Examiner*—Nancy Mulcare
*Attorney, Agent, or Firm*—Donald D. Mon

[57] ABSTRACT

A medical forceps has an elongated body, two handle elements at one side and two jaw parts at the other side of said elongated body. Actuating means serve for actuating said two jaw parts responsive to the movement of the two handle elements. The actuating means are designed in that within a first range of movement of said handle elements, said two jaw parts are pivoted together, and within a second range of movement of said handle elements, one of said two jaw parts is moved relative to the other one of said two jaw parts.

9 Claims, 9 Drawing Sheets

MEDICAL FORCEPS WITH JAWS WHICH FIRST TILT AND THEN OPEN

BACKGROUND OF THE INVENTION

The invention concerns a medical forceps having an elongated body with two handle elements disposed at a first end of said body, movable with respect to one another and two jaw parts disposed at a second end of said body nearest the patient which jaw parts can be moved relative to one another by means of said handles via actuating means.

A medical forceps of this kind is known from German Utility Model G 91 15 760.9. One of the two jaw parts is configured as a rigid jaw part whose alignment is such that, together with a tube-like elongated body that connects a handle element at the end remote from the patient with the rigid jaw part at the end nearest the patient, it encloses an acute angle opening toward the end remote from the patient.

The second jaw part, which is movable with respect to the first, moves toward the tube as the jaw parts open.

A problem of the aforementioned medical forceps is that although the dimensions of the components at the end nearest the patient are as small as possible, the hooked configuration of the rigid jaw part is very awkward.

One possible application for a medical forceps of this kind is to be introduced into a human maxillary sinus in order to remove a piece of tissue, for example a cyst, therein. The end of the medical forceps nearest the patient can be introduced into the maxillary sinus through the nasal opening and an opening provided in the nasal septum (called a "window"); local anesthesia is generally sufficient in such a procedure, so that a complex operation with general anesthesia, involving opening of the maxillary sinus from outside, is not necessary.

Although the angled arrangement of the jaw parts makes it possible to apply the jaw parts to the cyst being removed and to grasp it with the opened jaw parts, the detachment process itself is nevertheless relatively difficult to perform. Once the cyst has been grasped by the jaw parts, it is more or less torn off by moving the entire forceps. Moreover it is extremely difficult, because of the hooked configuration of the forceps at the end nearest the patient, to pull it back out of the maxillary sinus, since this entails a risk that it may catch on other tissues in an undesirable manner.

SUMMARY OF THE INVENTION

The object of the present invention is therefore to improve a medical forceps of the aforesaid type in such a way as to improve how the forceps is brought into position, and the procedure for detaching tissue.

According to the invention, the object is achieved by the fact that both jaw parts are arranged movably at the end of the forceps body nearest the patient. In a first range of movement of the handle elements both jaw parts can be pivoted together by means of the actuation means and that in a second range of movement of the handle elements one jaw part can be moved relative to the other jaw part.

These features have the substantial advantage that in the first movement range of the handle elements, the two jaw parts can be moved together, i.e. for example while closed against one another. This movability of the closed jaw parts thus makes it possible to move them, at the end of the forceps nearest the patient, to the most favorable point for bringing the end nearest the patient into position. Taking the example of the aforementioned process of introduction into the maxillary sinus, the jaw parts, closed against one another, can be brought into a position in which they can be inserted into the nose most favorably and with as little harm to the patient as possible, i.e. in as slender a configuration as possible. If an opening or window is present in the nasal septum, through which the jaw parts are to be introduced into the maxillary sinus, the closed jaw parts can be brought either into the same position in which they were introduced into the nose or, by suitable pivoting of the jaw parts together, into a favorable position such as to facilitate introduction into the maxillary sinus. Once the jaw parts of the forceps have been inserted into the maxillary sinus, for example to a location at which a cyst must be detached, the jaw parts, still closed, then can be brought either by rotating the entire forceps or by a further movement of the handle elements within the first range of movement into a position in which, for example as shown in the aforementioned German Utility Model, the still closed jaw parts forming an angle with the elongated body of the forceps. Because of the fact that in the second range of movement of the handle elements, one jaw part can be moved relative to the other jaw part, the two jaw parts can now be opened in order to grasp the tissue being detached, for example the cyst, and applied thereto. Once the tissue has been gripped by the jaw parts, they can be closed again by moving the handle elements correspondingly in the opposite direction, thus holding the tissue firmly. With a following moving of the handle elements within the first range of movement of the handle elements again, a considerable advantage of the invention becomes evident. The two jaw parts having gripped the tissue can now, in the first range of movement of the handle elements, both be moved or pivoted together, by merely moving the handle elements with no need of moving the entire medical forceps. The jaw parts having gripped the tissue move together away from the detachment point, thereby advantageously supporting the process of detaching the tissue. The combination of the features, i.e. that the jaw parts can move relative to one another, and simultaneously that the two jaw parts can pivot together with the tissue gripped between them, considerably facilitate the process of gripping and detaching the piece of tissue. When the medical forceps is subsequently withdrawn from the human body, the considerable advantage of being able to pivot the two jaw parts together is expressed in the fact that the said jaw parts, with the detached piece of tissue gripped therebetween, can be moved or pivoted into a position that facilitates withdrawal of the medical forceps from the human body.

The object is thus achieved completely.

In a further embodiment of the invention, both jaw parts are arranged pivotedly about a common shaft or axis at the end nearest the patient.

The advantage of this feature is that the two jaw parts are arranged pivotedly by means of a small number of components, namely the common shaft, which produces a space-saving and slender design at the end nearest the patient.

In a further embodiment of the invention, in the second movement range of the handle elements one jaw part is immobilized, and the other jaw part can move relative to the immobilized jaw part.

This feature also has the considerable advantage that the transition from movement of the pivotable jaw parts together to movement of the jaw parts relative to one another is made possible with simple means that are not bulky. Only one jaw part is immobilized, for example by a stop, so that the other jaw part can be moved further by means of the same actuation mechanism as with the previous movement.

In a further embodiment of the invention, the actuating means comprise an actuation element connected at one end to a handle element and at the other end connected in an articulated fashion to that jaw part that can also be moved in the second movement range.

The considerable advantage of this design feature is that only a single actuation element moves the jaw part that is moved further with respect to the immobilized jaw part, but at the same time it can also move the other jaw part when the jaw parts move together.

In a further embodiment of the invention, the jaw part that is immobilized in a fixed position in the second movement range can be moved, in the first movement range, against the force of a spring away from the immobilized position toward shared pivoting of the jaw parts, and in the opposite direction this spring force reinforces the shared movement of the two jaw parts together.

The considerable advantage of this feature is that, being directed from the immobilized position toward shared pivoting, this movement of the jaw part is performed against spring force, i.e. sufficient compression of the two jaw parts is present during shared pivoting. During this movement, a piece of tissue gripped by the jaw parts and detached is continuously held firmly and thus cannot be lost. In the opposite direction, i.e. when the jaw parts in contact with one another pivot toward the position in which one of the jaw parts is immobilized, the spring force has a positive reinforcing effect.

In a further embodiment of the invention, the jaw part that can be immobilized in a fixed position is connected in an articulated fashion to a control element, acted upon by a spring, which is movably mounted on the handle element that is not connected to the actuation element.

The considerable advantage of this feature is that the components generating the spring force can be arranged away from the end nearest the patient in the region of the end remote from the patient, where substantially more room is available, and that the spring force is transferred by means of the control element to the jaw part at the end nearest the patient. The arrangement of these components on the handle element on which the actuation element is not arranged then allows adjustment of the spring force on this other handle element entirely independently of the actuation element, so that a spring force that is optimal or convenient for the particular user of the medical forceps can be set.

In a further embodiment of the invention, the control element at the end remote from the patient is provided with an end piece on which the spring acts.

The advantage of this feature is that the aforementioned design embodiment of the spring force application is implemented with simple and robust design features, making the forceps not only more convenient to use but also more reliable.

In a further embodiment of the invention, the forceps is curved at the end nearest the patient.

The advantage of this feature is that for certain applications, the curvature provided immediately creates a tapered contour at the end nearest the patient, which is suitable for introduction into body orifices such as the nasal cavity. The additional pivotability of the jaw parts then makes it possible to implement individually a particular optimum orientation, or curvature and angling, of the components at the end nearest the patient, allowing optimum adaptation not only to the intended purpose but also to the particular anatomical conditions of the patient, so that the forceps that be introduced and removed, adapted to his or her anatomy, with as little harm to the patient as possible.

In a further embodiment of the invention, the forceps is an integral component of an endoscope.

The advantage of this feature is that in combination with the endoscope, the particular local conditions can be observed and thus the jaw parts can be brought into the optimum orientation.

It is understood that the features mentioned above and those yet to be explained below can be used not only in the combinations indicated, but also in other combinations and in isolation, without leaving the context of the present invention. The invention will be further described and explained below with reference to an exemplary embodiment. In the drawings,

DESCRIPTION OF THE PREFERRED EMBODIMENT

Figure 1:
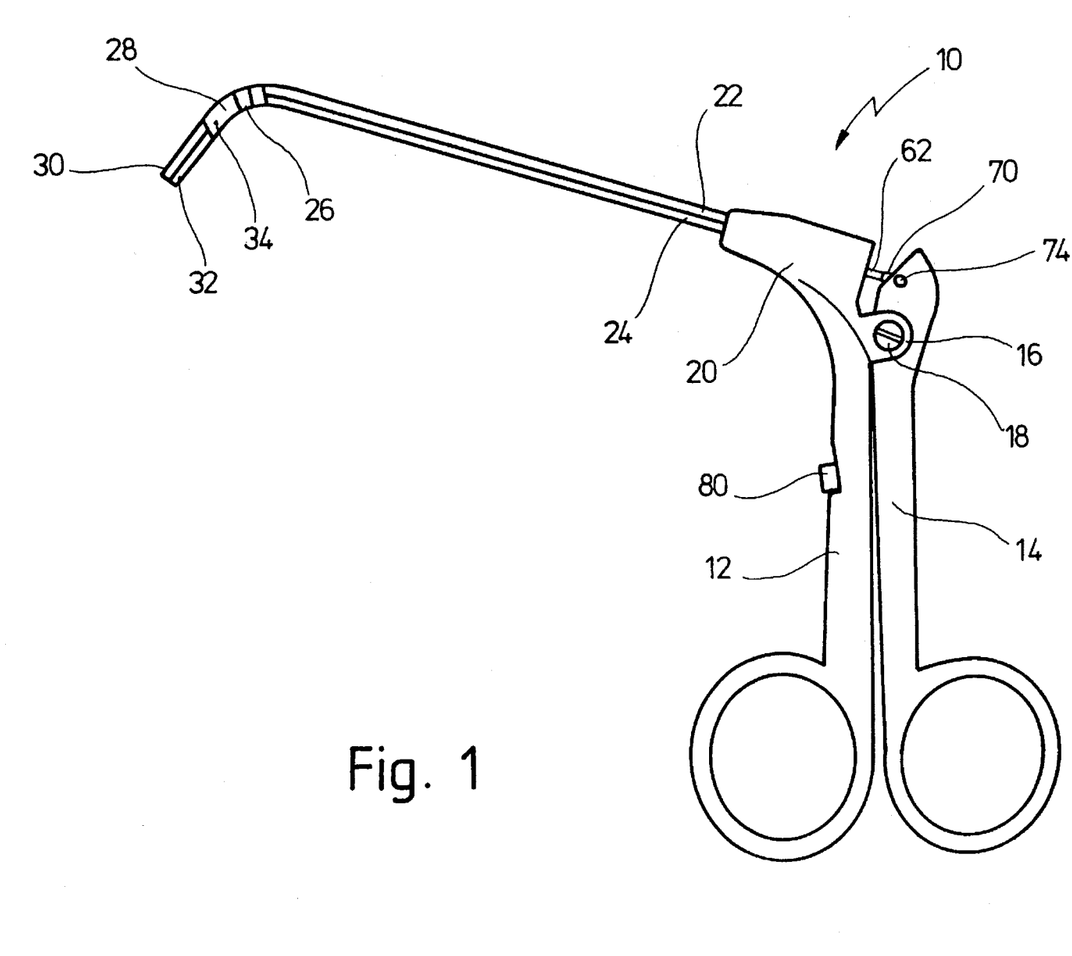
FIG. 1 shows a side view of a medical forceps according to the invention, in a first operating position with the jaw parts closed.

A medical forceps according to the invention, depicted in FIG. 1, is labeled in its entirety with the reference number 10.

The forceps 10 has two handle elements 12 and 14 that are connected to one another by a hinge 16. The connection is made by means of a screw 18, so that the two handle elements 12 and 14 can pivot relative to one another about the lengthwise center axis (not shown further here) of the screw 18. Extending from an upper end region 20 of the handle element 12 (see also in particular FIG. 2) are two closely adjacent tubes 22 and 24, each of which has an outside diameter of about 1.5 mm. The tubes can be made of steel or of a plastic material with comparable properties. The two tubes 22 and 24 provide an elongated body of the forceps 10.

At the end nearest the patient the two tubes 22, 24 end at approximately the same level (see in particular FIG. 3), and are connected to an end piece 26 whose outer end is configured as a fork 28. Arranged between the two outer tines of the fork 28 are two jaw parts 30, 32 that are accommodated pivotely within the fork 28 by means of a shared pivot pin 34. The center lengthwise axis of the pivot pin 34 thus represents a pivot axis for the two jaw parts 30, 32.

The jaw part 30 is connected to a control element 36 in the form of a wire 38, specifically by means of a pin 40 at the end of the wire 38, running perpendicular to its long axis. The wire is thus configured somewhat like the end of a Bowden cable. The pin 40 creates an articulated connection between the end of the wire 38 and the jaw part 30. As is evident in particular from FIG. 3, the pin 40 ends up at a distance from the pivot pin 34.

Figure 2:
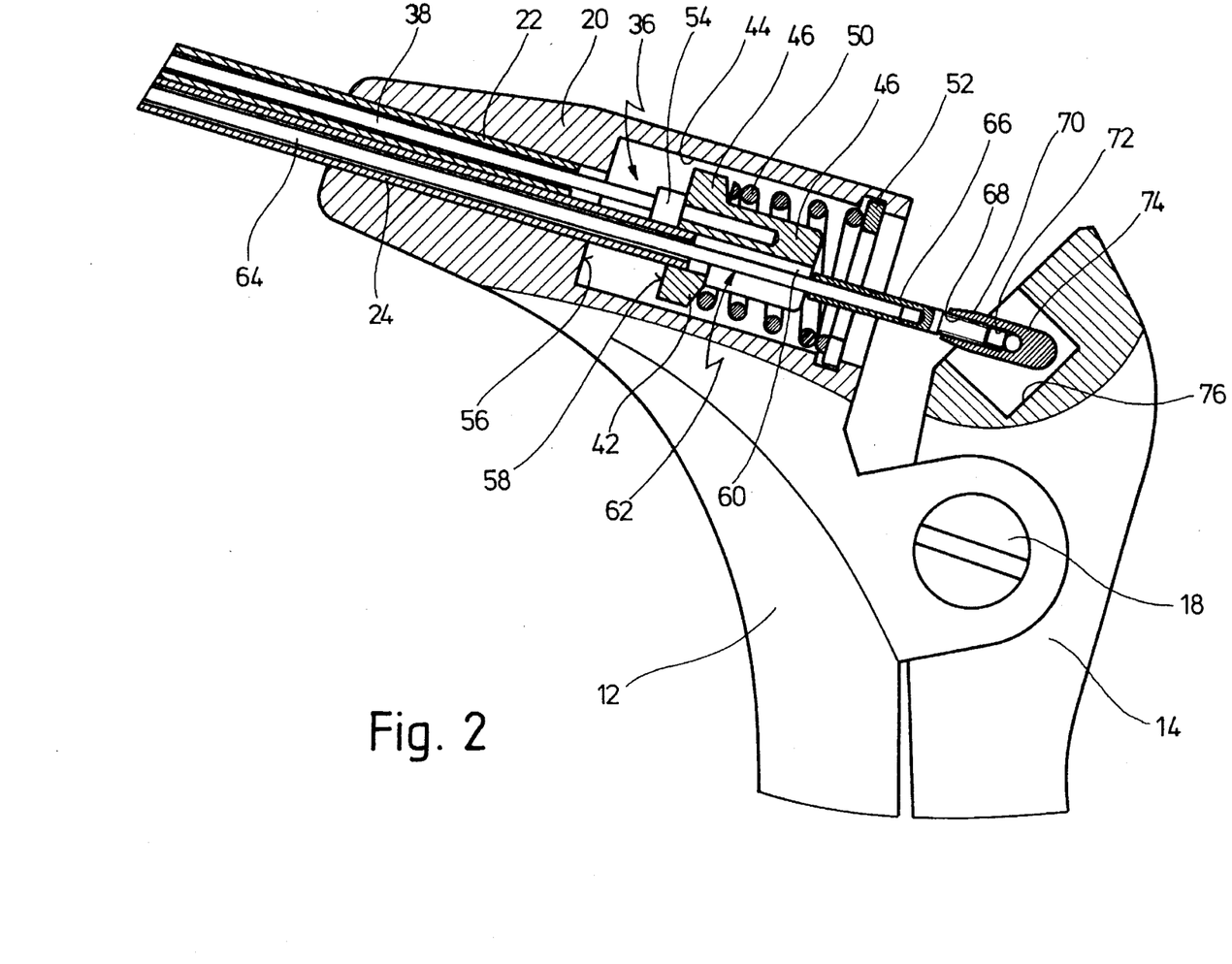
FIG. 2 shows a detailed, partial, and partly cut-away view of the medical forceps of FIG. 1 in the region of the handle elements.

The wire 38 is accommodated in the tube 22 and is permanently connected at its end opposite the pin 40 to an end piece 42 (see in particular FIG. 2). The end piece 42 is accommodated in a recess 44 in the end region 20 of the handle element 12, the recess 44 being configured as a blind hole into which the end piece 42 can be introduced.

Leading from a bottom surface or sidewall 56 of the recess 44 toward the end nearest the patient is a passthrough conduit (not characterized further here) in which the tubes 22 and 24 are arranged.

The end piece 42 has a blind hole (not characterized further here) in which an end piece of the wire 38 is accommodated, the wire 38 being connected in a lossproof manner to the end piece 42 by means of a clamp 54.

The end piece 42 has an annular flange section 46, facing the bottom surface 56 of the recess 44, that continues into a cylindrical section 48 with a smaller diameter. Arranged around the cylindrical section 48 is a helical spring 50 that braces against the upper annular surface of the annular flange section 46. At the opposite end, the helical spring 50 braces against a snap ring 52 that is inserted in an annular groove (not characterized further here) in the open end region of the recess 44.

The helical spring 50 is preloaded so that it has a tendency to push the end piece 42, in the position depicted in FIG. 2, toward the bottom surface 56 of the recess 44. Also provided in the end piece 42 is a through hole 60 through which an actuation element 62 extends movably.

The actuation element 62 has a wire 64 whose end region remote from the patient is permanently connected to an end sleeve 66 which projects beyond the end of the handle element 12 that is to the right in the depiction of FIG. 2. The end sleeve 66 is provided with external threads 68, and is threaded into a receptacle sleeve 70 provided with internal threads 72. The receptacle sleeve 70 is pivotedly installed in a recess 76 at the top end of the handle element 14 by means of a screw 74.

Figure 3:
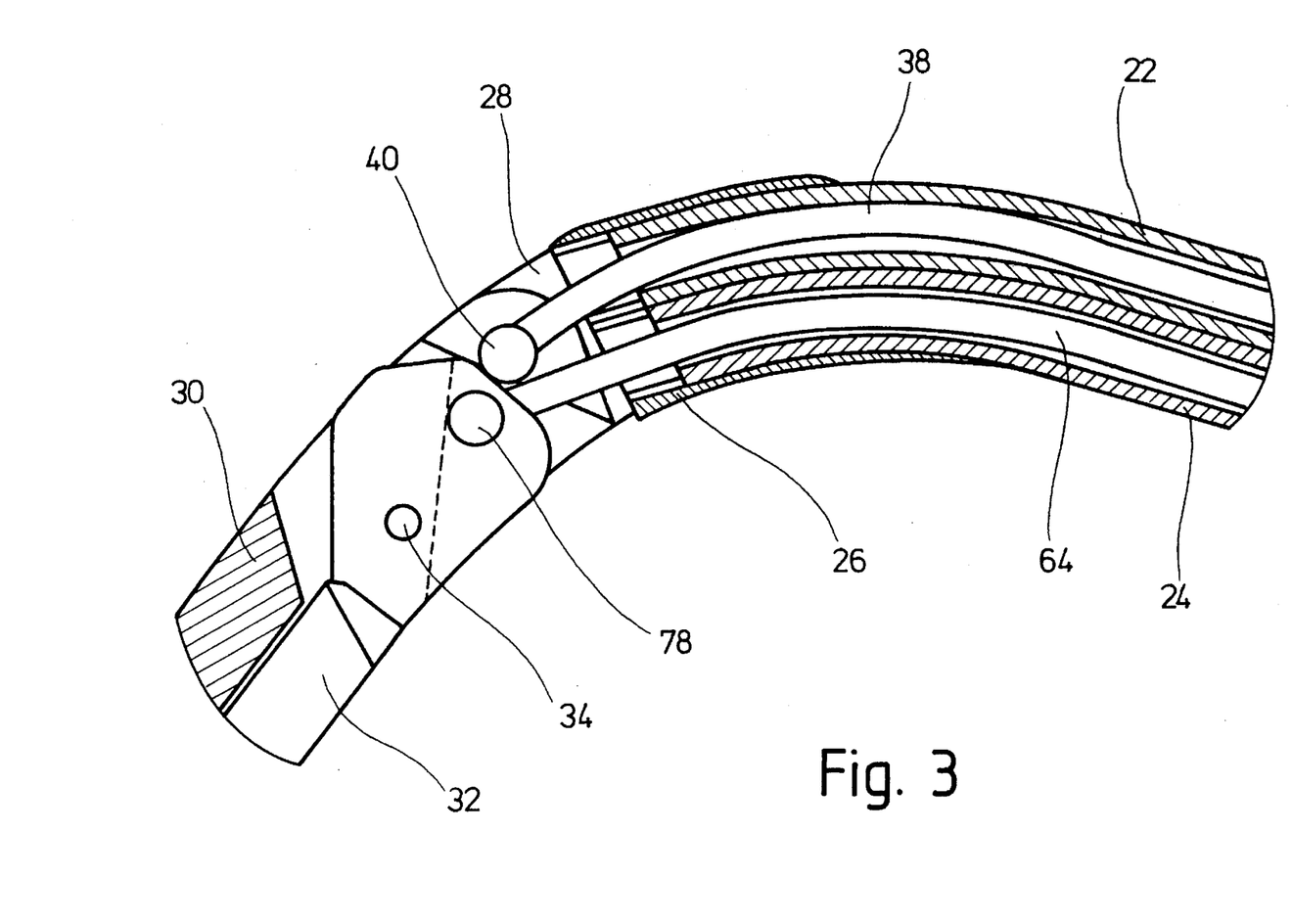
FIG. 3 shows an even further enlarged, partial, and partly cut-away depiction of the end region nearest the patient of the medical forceps of FIG. 1.

The wire 64 extends from the end sleeve 66 through the hole 60 in the end piece 42, and is guided through the tube 24 to the jaw part 32 (see FIG. 3). At this end nearest the patient, the wire 64 is connected in an articulated fashion to the jaw part 32 by means of a pin 78 that runs perpendicular to its long axis. The end region of the wire 64 is configured identically to the end region of the wire 38, as described above, and the pin 78 also ends up at a distance from the pivot pin 34 about which both jaw parts 30, 32 can pivot.

It is evident from FIG. 1 that a set screw 80 is provided on the handle element 12, allowing adjustment of the first operating position (depicted in FIG. 1) of the medical forceps 10.

It is also evident from FIG. 1 that the forceps 10 is curved at the end nearest the patient, i.e. in the region of the end piece 26, and then continues into the jaw parts 30, 32 which extend in a straight line in the exemplary embodiment depicted.

The jaw parts 30, 32 are configured as straight, approximately beam-shaped parts with cutting edges (not depicted further) resting against one another. As will be explained below, the jaw parts are used to grasp a piece of tissue, detach it, and hold the detached tissue between the jaw parts.

Numerous embodiments of the jaw parts 30, 32 are possible for this purpose. They can be configured as spoon-like nesting parts or they can be configured as knife-like cutters with union elements, provided only that the double function, namely detaching and holding the piece of tissue, is possible. Furthermore it is also possible to continue the jaw parts 30, 32, in accordance with the curvature depicted in FIG. 1, in a further curve in order, depending on the intended application, to ensure the simplest possible introduction of the end region nearest the patient through a body orifice, for example through a person's nasal orifice.

Figure 4:
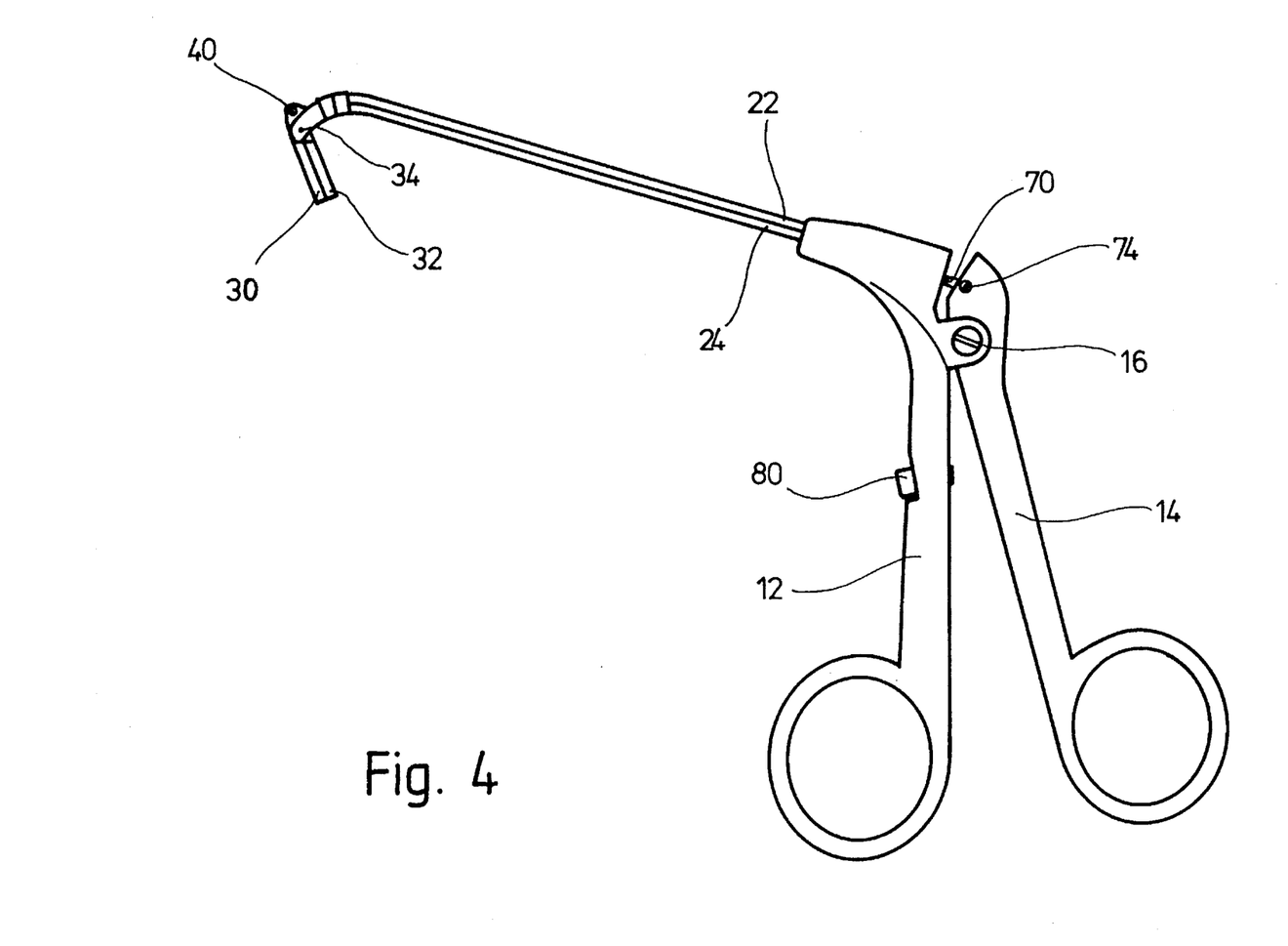
FIG. 4 shows a depiction, comparable to FIG. 1, of the medical forceps according to the invention in a second operating position with the jaw parts pivoted but still closed.
Figure 5:
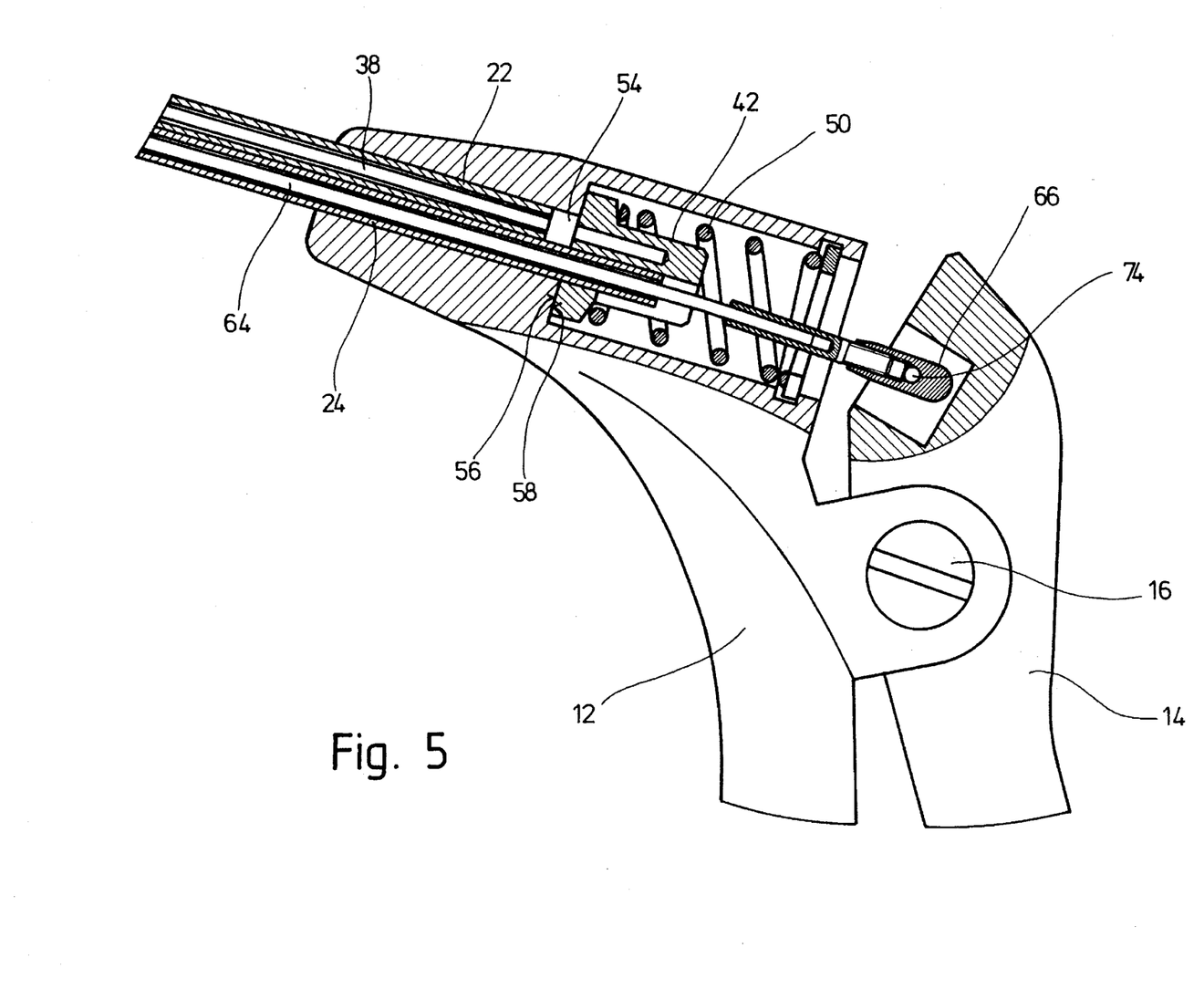
FIG. 5 shows a depiction comparable to the depiction of FIG. 2, in the second operating position.
Figure 6:
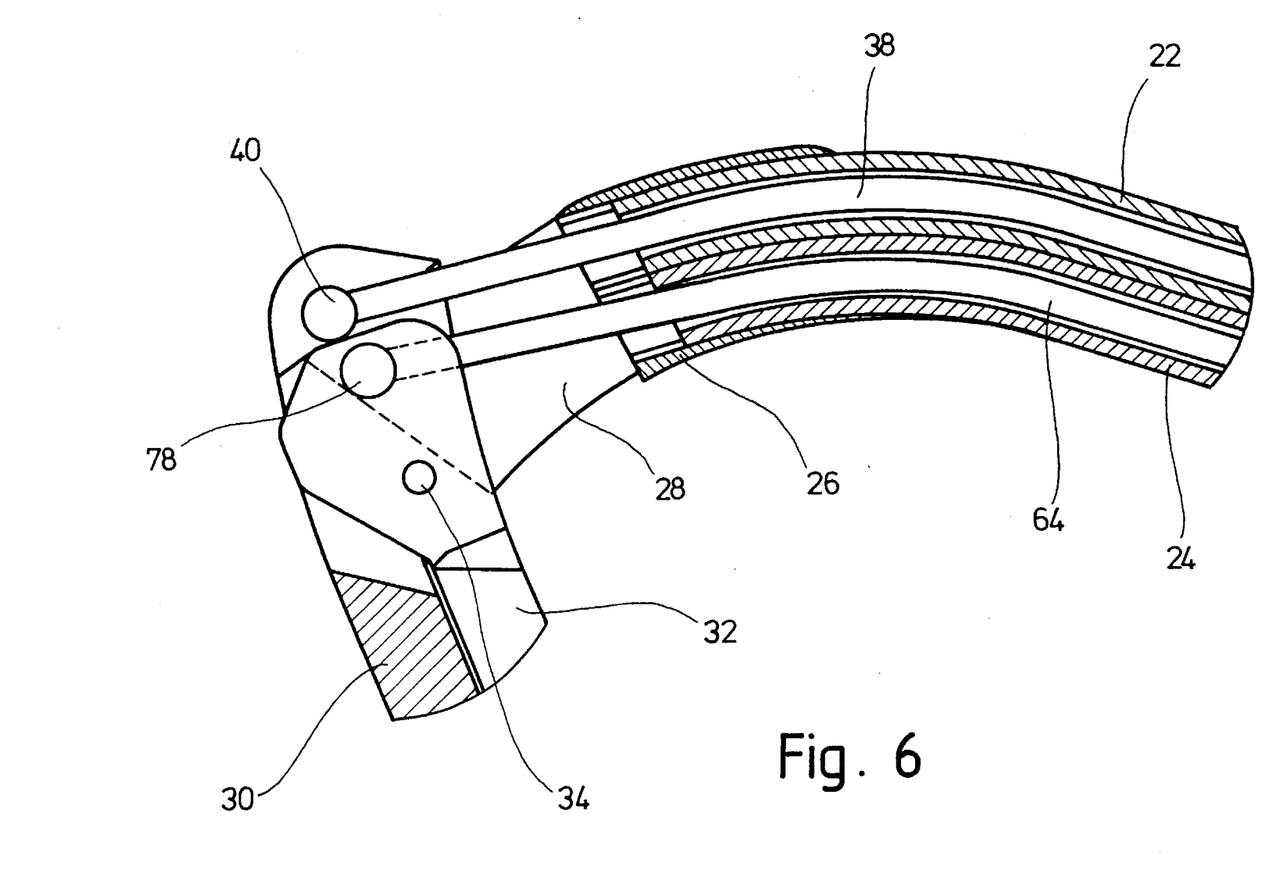
FIG. 6 shows a depiction comparable to FIG. 3, in the second operating position.

By opening the handle elements 12 and 14, the forceps 10 can be brought from the first operating position depicted in FIGS. 1 to 3 to the second operating position depicted in FIGS. 4 to 6.

During this movement the handle element 14, as depicted in FIGS. 1 and 4, is pivoted counterclockwise about the hinge 16. As a result the wire 64 is displaced through the tube 24 toward the end nearest the patient, thus causing the jaw part 32 to pivot, because of the articulated connection by means of the pin 78, about the pivot pin 34. The wire 38 follows the movement of the wire 64, this being reinforced by the force of the helical spring 50; in other words during this movement the end piece 42, and thus also the wire 38 permanently connected thereto, are also displaced by the helical spring 50 synchronously toward the end nearest the patient.

the jaw part 30 connected to the wire 38 does indeed remain closed against the jaw part 32 and thus cannot overtake it.

This shared pivoting of jaw parts 30 and 32 while closed against one another occurs until the end surface 58 of the end piece 42 contacts or abuts against the bottom surface 56 of the recess 44. This situation is depicted in FIG. 5. Further advance of the wire 38 is now blocked, i.e. the jaw part 30 is now blocked or immobilized from further counterclockwise pivoting.

With a further opening movement of the handle element 14, however, the wire 64 can be displaced further through the end piece 42 toward the end nearest the patient, which causes the jaw part 32 to move further relative to the immobilized jaw part 30 and to be pivoted about the pivot pin 34, so that the jaw parts 30, 32 move away from one another, i.e. are opened.

Figure 7:
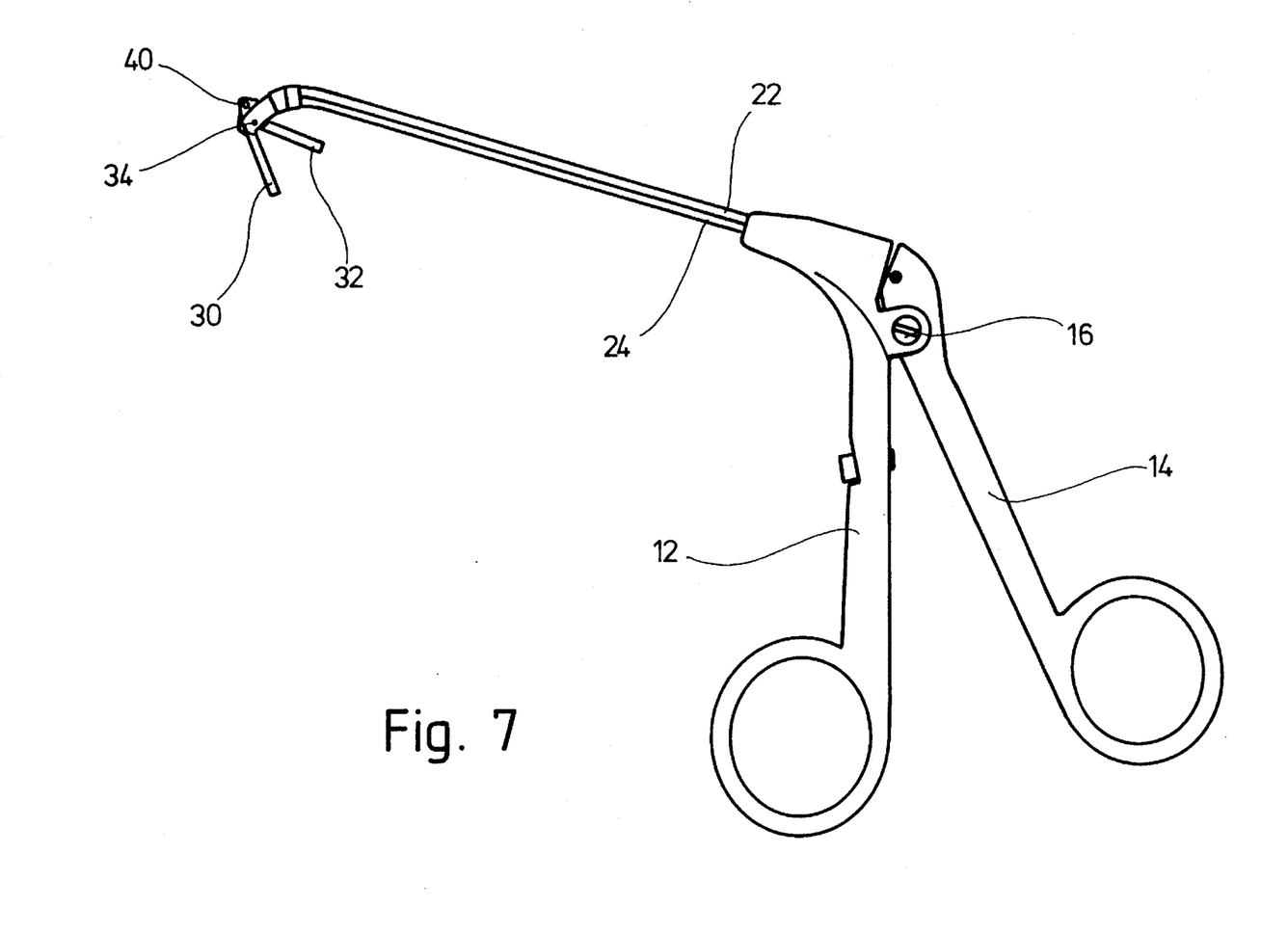
FIG. 7 shows a depiction, comparable to FIG. 1, of the medical forceps according to the invention in a third operating position with the jaw parts open.
Figure 8:
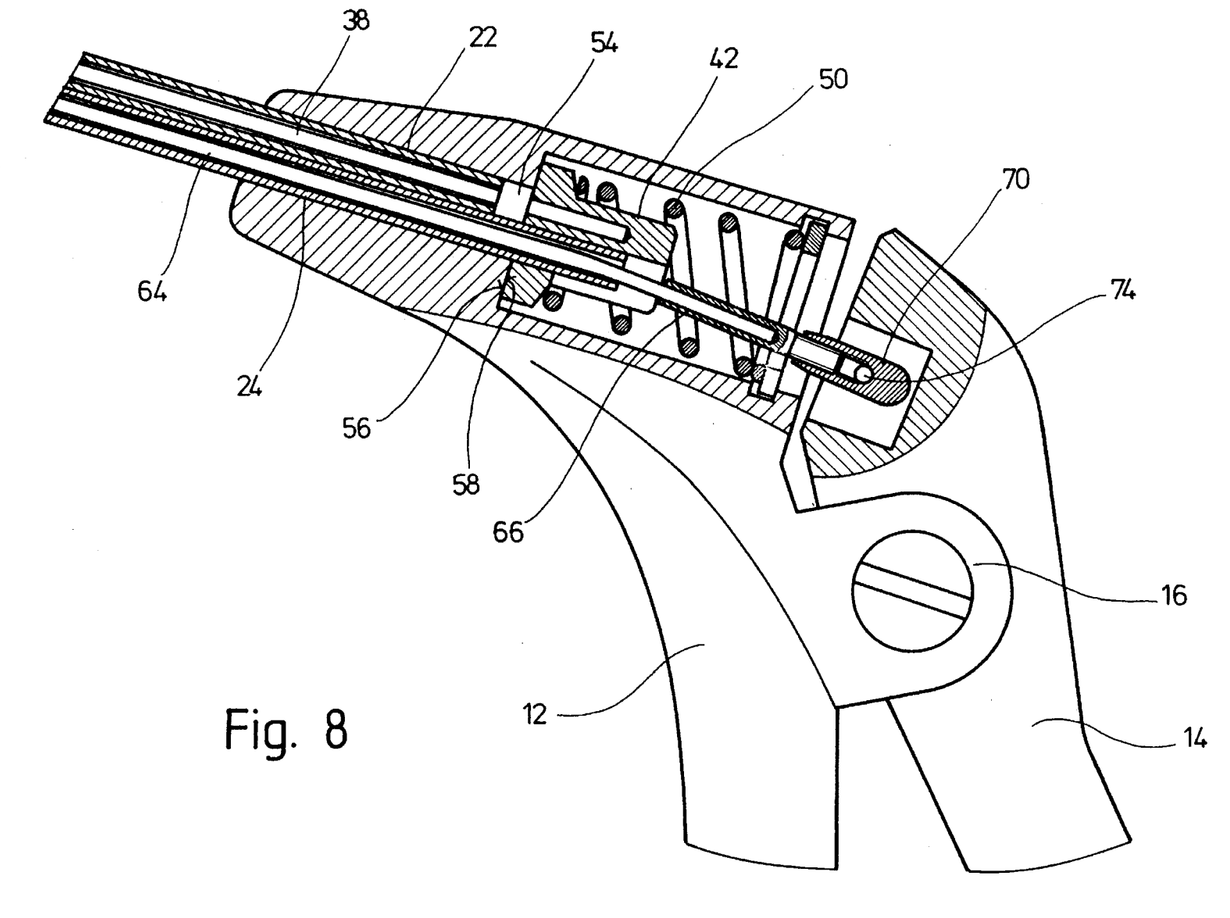
FIG. 8 shows a depiction comparable to FIGS. 2 and 5, in the third operating position.
Figure 9:
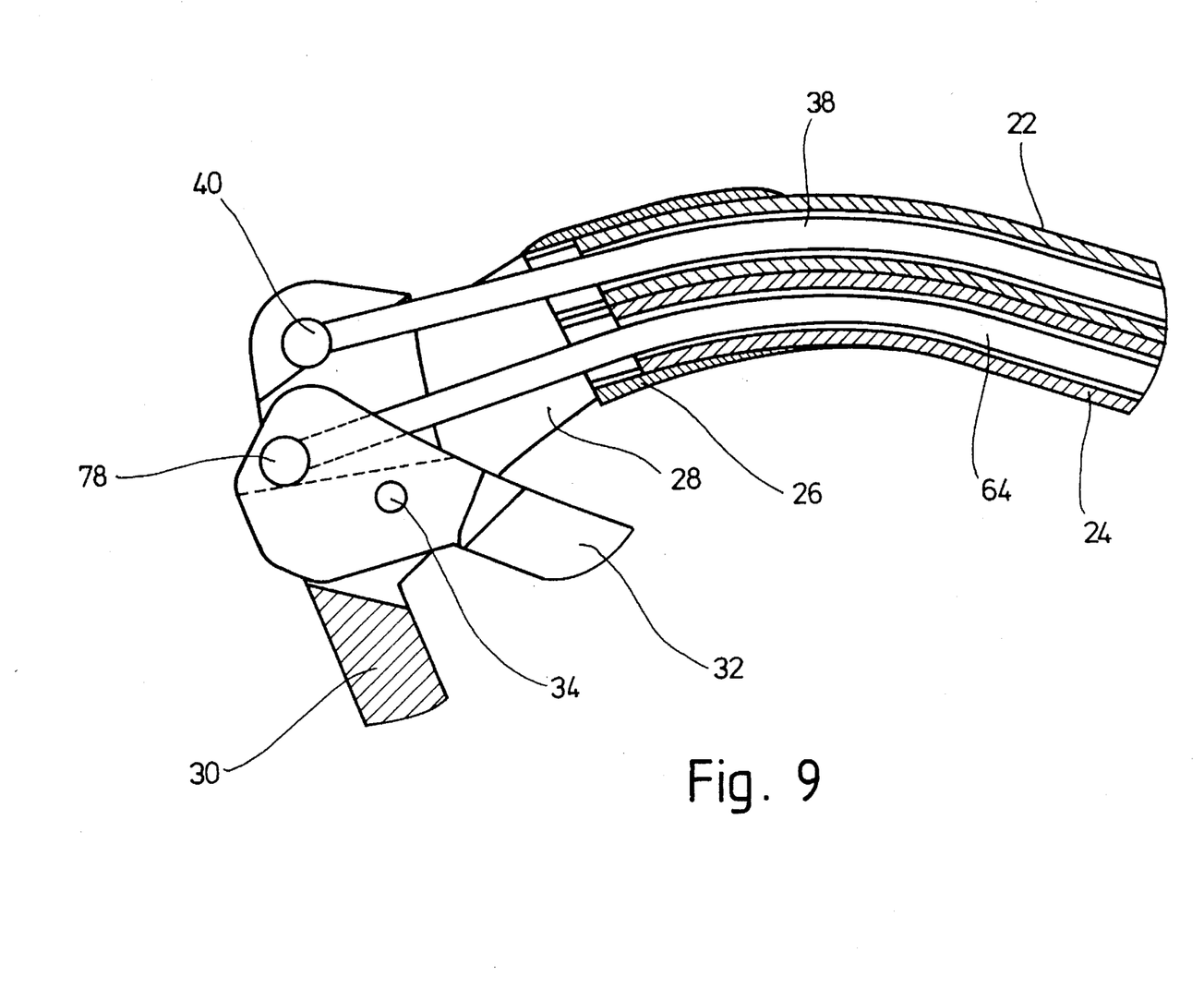
FIG. 9 shows a depiction comparable to FIGS. 3 and 6, in the third operating position.

Such a situation is depicted in FIGS. 7 to 9. In this third operating position the handle elements 12 and 14 are opened almost to their maximum extent; it is evident in particular from FIG. 8 that this is possible just until the upper end of the handle element 14 contacts the corresponding opposite end of the handle element 12.

In this position, with the jaw parts 30, 32 open, it is then possible to bring between them a piece of tissue to be grasped, and to grasp said piece of tissue by closing the handle elements 12 and 14, thereby closing the jaw parts 30 and 32.

The closing movement of the jaw parts 30 and 32 occurs until the resistance pressure of the piece of tissue grasped between the jaw parts 30 and 32 is greater than the force of the spring 52. When this is exceeded, the result of further closing of the handle elements 12 and 14 is that the end piece 42 is displaced to the right out of the position depicted in FIG. 8, i.e. is released from immobilizing contact, thus allowing shared pivoting of the jaw parts 30 and 32 clockwise about the pivot pin 34. The force of the spring 50 ensures that the jaw parts 30, 32 are held closed with suitable force, so that the piece of tissue grasped between them is held so firmly that, because of the pivoting movement, it is detached from the location from which it was taken. By closing the handle elements 12 and 14 further, the jaw parts 30 and 32 can then be brought into a position that allows the easiest possible withdrawal of the medical forceps from the removal point.

To allow the most accurate possible observation of the detachment process in situ, it is possible to attach the medical forceps 10 to an endoscope. For this purpose it is possible to lay an endoscope shaft alongside the tubes 22 and 24, and advance it to the point that its end region ends up in the region of the end piece 26, so that the removal point and the pivoting movement of the jaw parts 30, 32 can be precisely observed, and then controlled, through the endoscope. It is possible to design the forceps 10 as an integral component of an endoscope, or first to introduce the forceps and then to guide the endoscope in along the tubes 22 and 24.

I claim:

1. A medical forceps, comprising an elongated body having an axis two handle elements disposed at a first end of said body, said first end being remote from a patient to be treated by the medical forceps, said two handle elements being joined and pivotally movable one to another at said first end, two jaw parts disposed at a second end of said body, said second end being disposed opposite from said first end, actuating means for actuating said two jaw parts responsive to a pivotal movement of said two handle elements relative one to another, said jaws being pivotally joined to one another so as to be movable toward and away from one another, and being mounted as a pair to said body at said second end for simultaneous rotation as a unit in a plane which includes said axis, when said jaws are closed on one another, within a first range of movement of said handle elements relative one to another, and within a second farther range of movement of said handle elements, one of said two jaw is pivoted away from the other one of said two jaw parts.

2. The medical forceps according to claim 1, wherein both jaw parts are arranged pivotably about a common axis at said second end of said elongated body.

3. Medical forceps according to claim 1, wherein within said second range of movement of said handle elements, one of said two jaw parts is blocked against further rotation relative to the other jaw part, and said other one of said two jaw parts is pivoted relatively to the blocked jaw part.

4. The medical forceps according to claim 3, wherein said actuating means comprises an actuation element connected at one of its ends to one of said handle elements, and connected at another one of its ends in an articulated fashion to that said one jaw part being moved relatively to the blocked jaw part.

5. Medical forceps according to claim 4, wherein that jaw part which is blocked in the second range of movement of said handles, can be moved within said first range of movement against the force of a spring in a direction away from the blocked position towards the directions of movement of the two jaw parts together, said force of said spring assisting the movement of the two jaw parts together in the opposite direction.

6. The medical forceps according to claim 5, wherein said one of said two jaw parts that can be blocked in a fixed position is connected in an articulated fashion to a control element, which control element is mounted slidably on that one of said two handle elements not connected to the actuation element, and wherein said spring acts onto said control element.

7. Medical forceps according to claim 6, wherein an end piece is provided at one end of said control element, said one end is being located in a recess provided in said handle element not connected to the actuation element, said spring acting onto said end piece of said control element, said end piece abutting against a wall of said recess in said blocked position of said blocked jaw part.

8. Medical forceps according to claim 1, wherein said body is curved in the area of its second end near the patient.

9. Medical forceps according to claim 1, wherein the forceps is configured as an integral component of an endoscope.

* * * * *